United States Patent
Ko et al.

(10) Patent No.: US 9,267,879 B2
(45) Date of Patent: Feb. 23, 2016

(54) ELLIPSOMETER FOR DETECTING SURFACE

(71) Applicant: Samsung Electronics Co., Ltd., Suwon-Si, Gyeonggi-Do (KR)

(72) Inventors: Kang-woong Ko, Seoul (KR); Hyoung-Jo Jeon, Suwon-si (KR); Gil-Woo Song, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 14/291,764

(22) Filed: May 30, 2014

(65) Prior Publication Data
US 2015/0077750 A1    Mar. 19, 2015

(30) Foreign Application Priority Data

Sep. 17, 2013    (KR) .................. 10-2013-0111516

(51) Int. Cl.
| | |
|---|---|
| *G01J 4/00* | (2006.01) |
| *G01N 21/01* | (2006.01) |
| *G01B 11/08* | (2006.01) |
| *G01N 21/21* | (2006.01) |

(52) U.S. Cl.
CPC ........ *G01N 21/211* (2013.01); *G01N 2021/213* (2013.01); *G01N 2021/214* (2013.01)

(58) Field of Classification Search
CPC ......... G01J 4/00; G01N 21/21; G01N 21/211; G01B 11/0641
USPC ................... 356/369, 244, 638, 364; 250/225
See application file for complete search history.

(56) References Cited

U.S. PATENT DOCUMENTS

| | | | | |
|---|---|---|---|---|
| 5,042,951 A | * | 8/1991 | Gold .................. | G03F 7/70633 356/364 |
| 5,076,696 A | | 12/1991 | Cohn et al. | |
| 5,706,212 A | * | 1/1998 | Thompson ............... | G01J 4/00 250/339.09 |
| 5,956,147 A | * | 9/1999 | Jellison et al. ................ | 356/369 |
| 6,798,511 B1 | | 9/2004 | Zhan et al. | |
| 7,477,388 B1 | | 1/2009 | Liphardt et al. | |
| 7,489,399 B1 | | 2/2009 | Lee | |
| 2007/0201017 A1 | * | 8/2007 | Opsal et al. ................ | 356/237.2 |
| 2008/0117413 A1 | * | 5/2008 | Liphardt et al. ................ | 356/73 |
| 2010/0128268 A1 | * | 5/2010 | Dainty et al. ................. | 356/367 |
| 2011/0205554 A1 | * | 8/2011 | Opsal et al. .................... | 356/625 |
| 2012/0261580 A1 | * | 10/2012 | Herzinger et al. ............ | 250/353 |
| 2013/0021604 A1 | | 1/2013 | Sun | |

FOREIGN PATENT DOCUMENTS

| | | |
|---|---|---|
| KR | 20030055960 A | 7/2003 |
| KR | 20040043987 A | 5/2004 |
| KR | 20060016621 A | 2/2006 |
| KR | 20060117759 A | 11/2006 |
| KR | 20070054936 A | 5/2007 |
| KR | 20100064612 A | 6/2010 |

\* cited by examiner

*Primary Examiner* — Tarifur Chowdhury
*Assistant Examiner* — Sunghee Y Gray
(74) *Attorney, Agent, or Firm* — Harness, Dickey & Pierce, P.L.C.

(57) ABSTRACT

An ellipsometer for detecting a surface including a light source irradiating a substrate with light, a polarization unit polarizing the light irradiated from the light source and analyzing the polarized light, a detector measuring a light quantity of the polarized light passing through the polarization unit, and a driver rotating the detector by an azimuth angle as the substrate rotates in a direction of the azimuth angle direction may be provided.

12 Claims, 13 Drawing Sheets

WAVEFORM OF A' WHEN LIGHT IS INCIDENT IN DIRECTION A

WAVEFORM OF B' WHEN LIGHT IS INCIDENT IN DIRECTION B

ELLIPSOMETER FOR DETECTING SURFACE

CROSS-REFERENCE TO RELATED APPLICATIONS

This application is based on and claims priority under 35 U.S.C. §119 to Korean Patent Application No. 10-2013-0111516, filed on Sep. 17, 2013 in the Korean Intellectual Property Office, the disclosure of which is incorporated herein in its entirety by reference.

BACKGROUND

1. Field

The present inventive concepts relate to apparatuses for monitoring physical properties of a substrate through detection of polarization properties of light, which is irradiated from a wide-area light source and is transmitted through or is reflected from a surface, and/or control methods thereof.

2. Description of the Related Art

In general, measuring optical properties of a material and/or thicknesses of thin films is important in the fields of, for example, physics, chemistry, and material science. Particularly, in the semiconductor industry, various nano-film fabricating processes are used, and in order to evaluate the physical properties of the fabricated nano films, ellipsometers, which employ a nondestructive and contactless real-time measurement technology, have been widely used as measurement equipment for processes.

With the development of light sources, light detectors, and computers, the performance of ellipsometers has been greatly improved, and in accordance with the development of processes using thin films, the application of the ellipsometers have been greatly increased.

The ellipsometers may be classified into a reflection type and a transmission type. Between the two types, the reflection type ellipsometer, which analyzes the polarization state of light that has an incident angle and is reflected from a surface of a test piece, has been widely used.

According to the reflection type ellipsometer technology, because parallel light is incident in a tilt direction, the incident angle can be accurately controlled. Thus, measurement is relatively accurate. However, if the size of incident beams is reduced through an iris, diffraction phenomenon may increase, and thus further reducing the size of the beams irradiated onto the test piece to mm or less may be challenging.

In the semiconductor industry, in order to evaluate various thin film fabricating processes for manufacturing semiconductor devices through measurement(s), a measurement region having a dimension of several tens of μm*several tens of μm is prepared on a wafer. In order to measure the physical properties of the measurement region, technology for focusing light on the surface of the test piece provided in the measurement region is used.

With the continuous development of semiconductor device fabricating technology, the size of a test piece patterned on a wafer is continuously reduced. Thus, the area of the limited measurement region is also reduced in proportion to the size of the test piece. However, in spite of intense research and effort, it has been difficult to further reduce the beam size of incident light due to technical barriers, for example, aberration and limitations of focal optical systems.

Recently, research has been made with respect to surface detecting ellipsometers, which measure the physical properties of a measurement region using the polarization properties of light irradiated from a wide-area light source and transmitted through or reflected from a surface.

SUMMARY

At least one example embodiment of the present inventive concepts provides an ellipsometer for detecting a surface, which can measure physical properties of a substrate by rotating a detector by an azimuth angle when the substrate is rotated in an azimuth angle direction.

At least one example embodiment of the present inventive concepts provides an ellipsometer for detecting a surface, which can discriminate between an active region and an inactive region of a substrate, perform masking of the inactive region, and operate not to collect data related to the inactive region.

Additional advantages, subjects, and features of the inventive concepts will be set forth in part in the description which follows and in part will become apparent to those having ordinary skill in the art upon examination of the following or may be learned from practice of example embodiments.

In an example embodiment of the present inventive concepts, an ellipsometer for detecting a surface includes a light source configured to irradiate a substrate with light, a polarization unit configured to polarize the light irradiated from the light source and analyze the polarized light, a detector configured to measure a light quantity of the polarized light passing through the polarization unit, and a driver configured to rotate the detector in accordance with an azimuth angle at which the substrate or the light rotates.

The ellipsometer may further include a controller configured to control the driver.

The polarization unit may include a polarization generator configured to polarize the light irradiated from the light source and output the polarized light to the substrate, and a polarization analyzer configured to analyze a change of a vibration direction of the polarized light reflected from the substrate and divide the polarized light that is reflected from the substrate into coordinate components.

The detector may include a 2D area image sensor including one of a CMOS (Complementary Metal-Oxide Semiconductor) and a CCD (Charge Coupled Device).

The ellipsometer may further include a monochrometer between the light source and the polarization generator and configured to select a wavelength range of the light irradiated from the light source.

The ellipsometer may further include a compensator between the polarization generator and the substrate and configured to adjust a polarization state of the light.

In an example embodiment of the present inventive concepts, an ellipsometer for detecting a surface includes a light source configured to irradiate a substrate with light, a polarization unit configured to polarize the light irradiated from the light source and analyze the polarized light, a detector configured to measure a light quantity of the polarized light passing through the polarization unit, through a sensor, a memory configured to store reference information on a pattern on the substrate, and a controller configured to determine at least one of pixels that can be sensed by the sensor and an activated sensing region of the sensor based on the reference information stored in the memory.

The polarization unit may include a polarization generator configured to polarize the light irradiated from the light source and output the polarized light to the substrate, and a polarization analyzer configured to analyze a change of a vibration direction of the polarized light reflected from the substrate and divide the polarized light that is reflected from the substrate into coordinate components.

The detector may include a 2D area image sensor including one of a CMOS (Complementary Metal-Oxide Semiconductor) and a CCD (Charge Coupled Device).

The reference information stored in the memory is pixel information corresponding to a pattern formed on the substrate.

The controller may be configured to control the pixels that can be sensed by the sensor with respect to the reference information.

The reference information stored in the memory is information with regard to a pattern formed on the substrate.

The controller may be configured to determine an active region and an inactive region of the sensor based on the reference information.

The ellipsometer may further include a monochrometer between the light source and the polarization generator and configured to select a wavelength range of the light irradiated from the light source.

The ellipsometer may further include a compensator between the polarization generator and the substrate and configured to adjust a polarization state of the light.

In an example embodiment of the present inventive concepts, an ellipsometer for detecting a surface includes a light source, a polarization unit configured to polarize light from the light source and irradiate the light onto a substrate, a detector configured to measure a light quantity reflected from the substrate, and a driver configured to rotate the detector in accordance with an azimuth angle at which the substrate or the light rotates.

The ellipsometer may further include a controller, which is configured to control the driver to rotate the detector in accordance with the azimuth angle.

The ellipsometer may further include a memory configured to store a map indicating a pattern on the substrate, wherein the detector is configured to measure the light quantity while masking information from the inactive region based on the masking map data.

The ellipsometer may further include a controller configured to determine pixels that can be sensed by the sensor based on the map.

The ellipsometer may further include a controller configured to determine an activated sensing region of the sensor based on the map.

If the region to be measured, which is prepared on the substrate, is not circular, the change of the geometrical shape of the region to be measured, which is projected onto the detector as the azimuth angle of the substrate rotates along the azimuth angle, may not be compensated for as in the case of an optical shape. According to the present inventive concepts, the detector is controlled to rotate by the same azimuth angle, thereby maintaining the effective measurement region thereof.

Further, because only the region, of which the measurement is required, of the whole region is measured and the remaining region is masked so as not to store the related data, the actual amount of measurement data can be reduced, thereby shortening the measurement time.

Because the amount of data to be processed can be reduced or minimized when the detector rotates and/or the inactive region is masked, data transfer time can be shortened. Consequently, the whole measurement time can be shortened.

BRIEF DESCRIPTION OF THE DRAWINGS

The above and other objects, features and advantages of the present inventive concepts will be more apparent from the following detailed description taken in conjunction with the accompanying drawings, in which.

DETAILED DESCRIPTION

Figure 1:
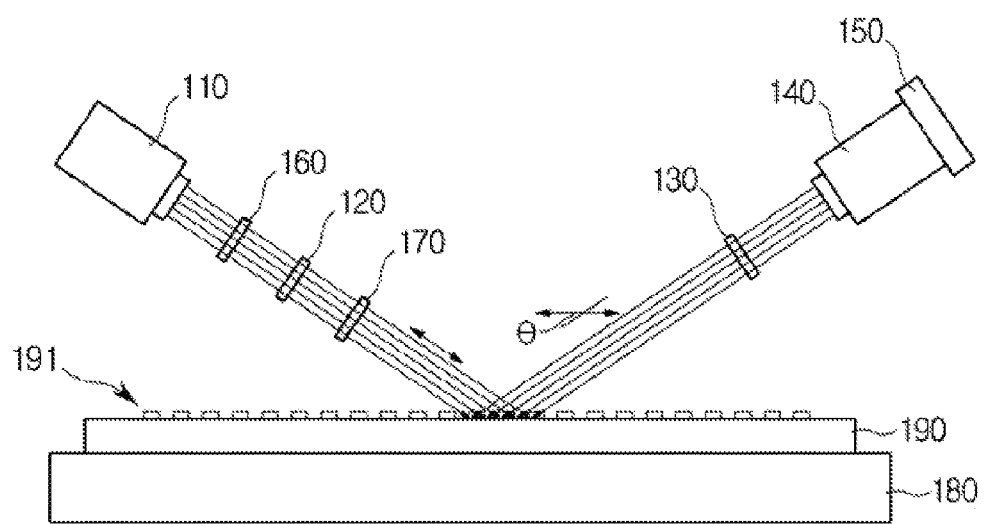
FIG. 1 is a view illustrating an example of the structure of an ellipsometer for detecting a surface, in which a detector is rotatable, according to an example embodiment of the present inventive concepts.

Various example embodiments will now be described more fully hereinafter with reference to the accompanying drawings, in which some example embodiments are shown. Example embodiments may, however, be embodied in different forms and should not be construed as limited to the example embodiments set forth herein. Rather, these example embodiments are provided so that this disclosure will be thorough and complete, and will filly convey the scope of example embodiments to those skilled in the art. The same reference numbers indicate the same components throughout the specification. In the attached figures, the thicknesses of layers and regions may have been exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of example embodiments. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments. It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless defined otherwise, all technical and scientific terms used herein have the same meaning as commonly understood by one of ordinary skill in the art to which this invention belongs. It is noted that the use of any and all examples, or example terms provided herein is intended merely to better illuminate the invention and is not a limitation on the scope of the invention unless otherwise specified. Further, unless defined otherwise, all terms defined in generally used dictionaries may not be overly interpreted.

The present invention will be described with reference to perspective views, cross-sectional views, and/or plan views, in which some example embodiments are shown. Thus, the profile of an example view may be modified according to manufacturing techniques and/or allowances. That is, the example embodiments are not intended to limit the scope of example embodiments, but cover all changes and modifications due to changes in manufacturing processes. Thus, regions shown in the drawings are illustrated in schematic form and the shapes of the regions are presented simply by way of illustration and not as a limitation.

Hereinafter, ellipsometers for detecting a surface according to some example embodiments will be described in detail with reference to the accompanying drawings.

An ellipsometer is a device that measures physical properties of an object using polarization phenomenon of transmitted or reflected light.

The ellipsometer for detecting a surface according to an example embodiment of the present inventive concepts may include a light source, a polarization unit polarizing light irradiated from the light source and dividing the polarized light, a detector measuring light quantity of the polarized light that passes through a polarization analyzer, and a driver rotating the detector. The ellipsometer may further include a controller controlling the rotation operation of the driver so that the detector is rotated by a calculated azimuth angle of a substrate.

The polarization unit may include a polarization generator polarizing the light irradiated from the light source and outputting the polarized light to the substrate, and the polarization analyzer provided to analyze a change of a vibration direction of the polarized light that is reflected from the substrate and to divide the polarized light that is reflected from the substrate into coordinate components.

Unlike a focus type ellipsometer, the ellipsometer for detecting a surface according to the present inventive concepts does not use a light transmitted through or reflected from a small spot region, but uses a light source having a wide area. For example, the ellipsometer according to the present inventive concepts detects the polarization properties of light that is transmitted through or is reflected from a surface using an area image sensor, and measures the physical properties of a measurement region, such as uniformity of a pattern using the detected polarization properties.

FIG. 1 is a view illustrating an example of an ellipsometer for detecting a surface, in which a detector is rotatable, according to an example embodiment of the present inventive concepts.

Referring to FIG. 1, an ellipsometer for detecting a surface according to an embodiment of the present inventive concepts includes a light source 110, a polarization generator 120, a polarization analyzer 130, a detector 140, a driver 150, and a controller (not illustrated).

The ellipsometer for detecting a surface according to an example embodiment of the present inventive concepts may further include a monochrometer 160 provided between the light source 110 and the polarization generator 120 and a compensator 170 provided between the polarization generator 120 and a substrate 190.

A stage 180 may move the substrate 190 to a place where the substrate 190 is to be attached by adjusting the stage 180.

Figure 2:
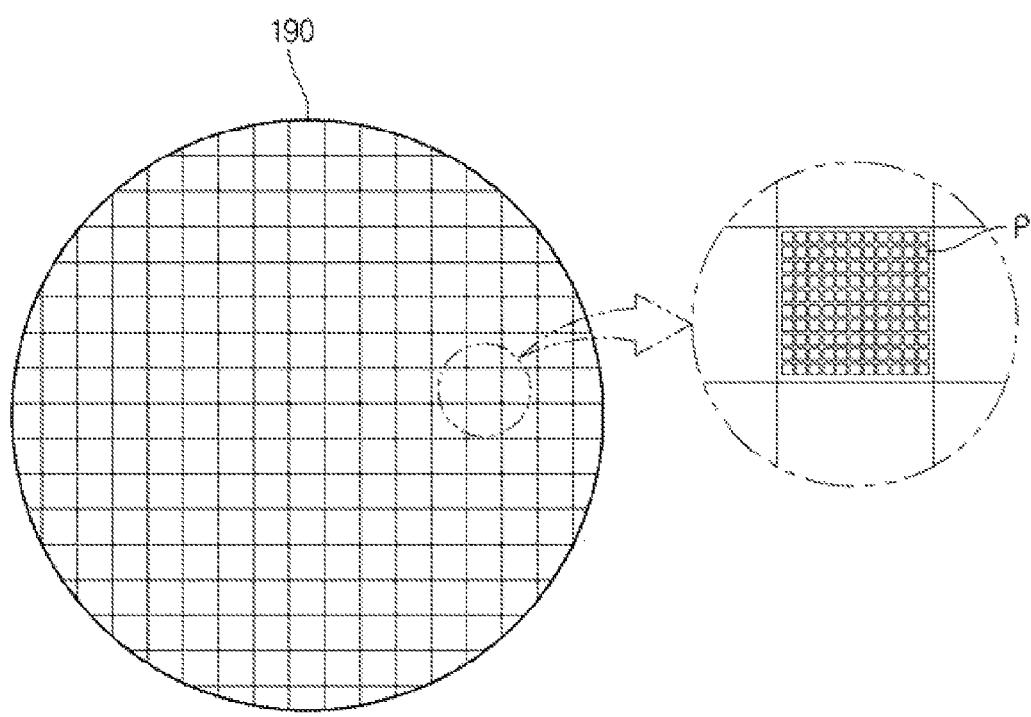
FIG. 2 is a view illustrating a pattern formed on the surface of a substrate to be measured by an ellipsometer for detecting a surface according to an example embodiment of the present inventive concepts.

The substrate 190 may include a wafer, and a regular pattern P as illustrated in FIG. 2 may be formed on the substrate 190.

The ellipsometer for detecting a surface according to an example embodiment of the present inventive concepts may be used to measure the physical properties of the pattern P that is formed on the substrate 190, and may be used to measure the uniformity of the pattern P that is formed on the substrate 190. Explanation will be made with respect to a case where the uniformity of the pattern, for example, the pattern P illustrated in FIG. 2, is measured.

The light source 110 is provided to irradiate the substrate 190 with light in order to measure the uniformity of the pattern P, which is formed on the substrate 190, and the light source 110 of the ellipsometer for detecting a surface according to an example embodiment of the present inventive concepts irradiates white light.

The monochromer 160 may be provided between the light source 110 and the polarization generator 120. The monochromer 160 is a device that extracts monochromatic light of a desired wavelength range from the white light. According to an example embodiment of the present inventive concepts, the monochromer 160 may extract visible light having a wavelength in the range of 3500 to 8000 Å.

The polarization generator 120 is arranged on an upper portion of the substrate 190 and on a traveling path of the light output from the light source 110. If the light output from the light source 110 is vertically incident to an incident surface of the polarization generator 120, polarized light having a specific vibration direction may be generated.

Figure 3:
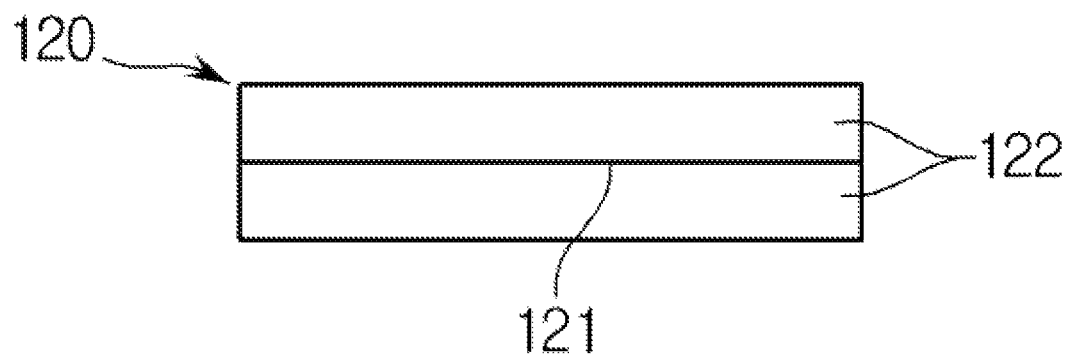
FIG. 3 is a view illustrating the structure of an ellipsometer for detecting a surface according to an example embodiment of the present inventive concepts.

As illustrated in FIGS. 1 and 3, the polarization generator 120 may include a polarization plate, which is manufactured by attaching optical glass or crystal 122 to both surfaces of a polarization film 121. A protection cover (not illustrated) composed of general optical glass may be additionally mounted in front of the polarization generator 120.

The protection cover (not illustrated) may be mounted vertically to the traveling direction of the polarized light so that the polarized light generated from the polarization generator 120 can vertically passes therethrough.

The compensator 170 may be provided between the polarization generator 120 and the substrate 190 and on the traveling path of the light output from the light source 110.

The compensator 170 is a device for optionally adjusting the polarization state of the light incident to the substrate 190. The ellipsometer for detecting a surface according to an example embodiment of the present inventive concepts may further include the compensator 170 to change a phase of a traveling wave in accordance with the polarization state.

The polarized light transmitted through the compensator 170 may have a specific phase difference value in accordance with a vibration direction of the polarized light, and the accuracy of the measurement can be improved through an adjustment of the compensator 170.

The polarized light goes straight and reaches the substrate 190 after passing through the polarization generator 120 and the compensator 170, and the light that has reached the substrate 190 is reflected by the pattern P formed on the substrate 190. The reflected polarized light goes straight and reaches the polarization analyzer 130.

In this case, the vibration direction of the polarized light incident to the substrate 190 changes in accordance with the pattern P that is formed on the substrate 190.

Referring to FIG. 1, the vibration direction of the polarized light that vibrates in parallel to an optical axis of the incident light may be changed at an angle of θ with the optical axis of the reflected light in accordance with the pattern P formed on the substrate 190, and the angle of θ may be changed in accordance with the shape of the pattern P and the incident angle.

The polarization analyzer 130 is arranged on the upper portion of the substrate 190, and more specifically, on the traveling path of the polarized light reflected from the substrate 190. The polarization analyzer 130 analyzes the changed vibration direction θ through separation of the light reflected from the substrate 190 into two or three polarized lights, of which the vibration directions are vertical to each other.

Hereinafter, an analyzing process performed by the polarization analyzer 130 according to an example embodiment of the present inventive concepts will be described in detail.

If it is assumed that the vibration direction of a wave of the polarized light generated by the polarization generator 120 is an X-axis direction, the wave that vibrates in the X-axis direction is reflected from the substrate 190, and thus the vibration direction thereof changes. The polarized light, of which the vibration direction changes, is vertically incident to the polarization analyzer 130, and the polarization analyzer 130 separates the wave into an X-axis component and a Y-axis component, or into an X-axis component, a Y-axis component, and a Z-axis component.

Figure 4A:
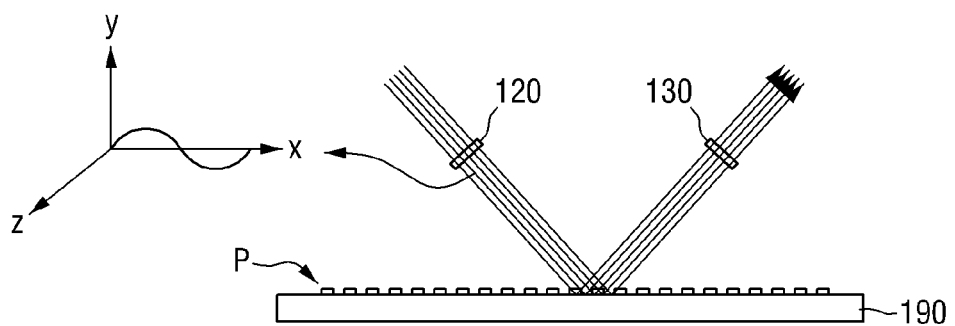
FIG. 4A is a graph illustrating the vibration direction of a wave when light passes through a polarization generator.
Figure 4B:
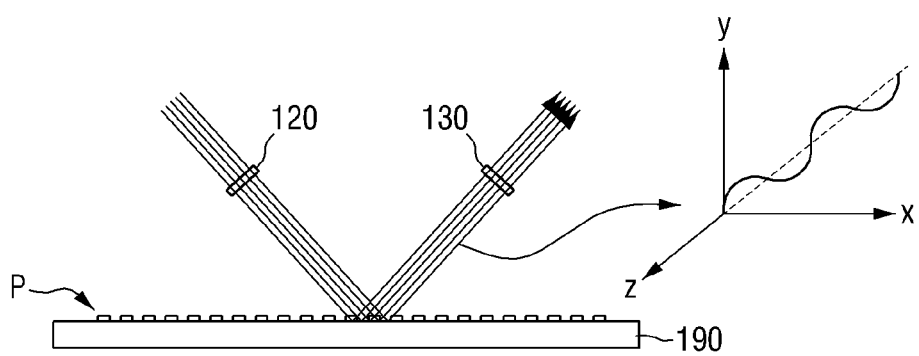
FIG. 4B is a graph illustrating the change of the vibration direction of a wave when light that is polarized through the polarization generator is reflected from a substrate.
Figure 4C:
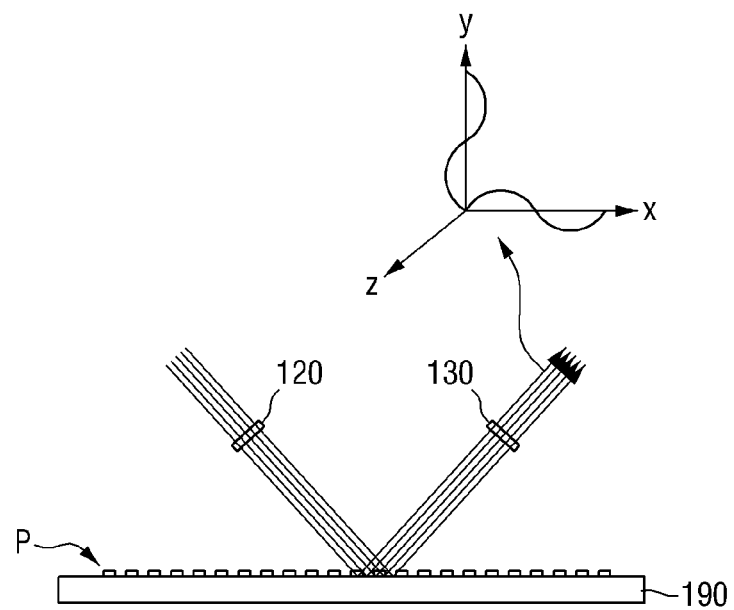
FIG. 4C is a graph illustrating the vibration direction of a separated wave when the wave of the polarized light, of which the vibration direction is changed, is separated through a polarization analyzer.

This will be described in more detail with reference to FIGS. 4A to 4C. FIG. 4A is a graph illustrating the vibration direction of a wave when light passes through the polarization generator 120. FIG. 4B is a graph illustrating the vibration direction of the wave that is reflected when the polarized light is reflected by the pattern P that is formed on the substrate 190. FIG. 4C is a graph illustrating the vibration direction of the wave when the wave of the polarized light, the vibration direction of which changes, is separated through the polarization analyzer 130.

Referring to FIGS. 4A to 4C, the light that has passed through the polarization generator 120 is polarized in the X-axis direction to vibrate (see FIG. 4A), and if the light that is polarized in the X-axis direction is incident to and then is reflected from the pattern P formed on the substrate 190, the polarization direction of the light changes (see FIG. 4B).

FIG. 4B may show different shapes of polarized light in accordance with the physical properties including the shape of the pattern P formed on the substrate 190. By analyzing the reflected polarized light as illustrated in FIG. 4B through the polarization analyzer 130, the polarized light may be separated into the X-axis component and the Y-axis direction as illustrated in FIG. 4C.

The detector 140 is provided in the rear of the polarization generator 120. The detector 140 measures the light quantity (e.g., intensity) of the polarized light analyzed by the polarization analyzer 130. More specifically, the detector 140 may receive the analyzed polarized light, generate charges that correspond to the quantity of received light, and outputs the charge as a received light output.

In the detector 140 according to an example embodiment of the present inventive concepts, a 2D area image sensor, such as a CMOS (Complementary Metal-Oxide Semiconductor) or a CCD (Charge Coupled Device), may be used.

The CMOS is a low power consumption image pickup device having a complementary metal oxide semiconductor structure, and the CCD is a device that sequentially transfers signal charge using electric potential wells that are created on a semiconductor surface by CCD transfer electrodes.

The 2D area image sensor uses the above-described device as a register, and photosensitive pixels that convert a light signal into a charge signal are provided in the register. The 2D area image sensor is composed of unit elements (pixels), and information acquired by the unit elements is transferred to the controller to be stored as a digital signal.

The driver 150 is provided on the rear surface of the detector 140. The driver 150 may rotate the detector 140 with respect to the optical axis while maintaining the optical axis of the detector 140. The installation purpose and the driving principle of the driver 150 will be explained in detail in the following description of the controller.

The controller may extract the optical properties of the pattern P through analysis of the waveform of a voltage or current detected by the detector 140.

Hereinafter, the principle of the controller will be described in detail.

The ellipsometer for detecting a surface according to an example embodiment of the present inventive concepts may be used to monitor various thin film fabricating processes for manufacturing semiconductor devices. For example, the ellipsometer may be used to measure whether a thin film is uniformly deposited in a measurement region, which is, for example, limited to an area of several tens of µm*several tens of µm, on a wafer.

In order to measure whether the thin film is uniformly deposited, the controller according to an example embodiment of the present inventive concepts may store a reference waveforms of voltage and/or current that should be detected by the detector 140 in accordance with the incident light when the thin film is uniformly deposited. Through this, if the surface of the substrate 190 is measured by the ellipsometer for detecting a surface and the waveform of the voltage and/or current in accordance with the pattern P is detected through the detector 140, the controller may determine the uniformity of the thin film through comparison of the detected waveform of the voltage and/or current with the reference (or alternatively, desired or pre-stored) waveform of the voltage and/or current.

The controller compares the measured waveform with the reference waveform in the range of 3500 to 8000 Å. If the measured waveform is within a desired (or alternatively, predetermined) reference range, the controller determines that a test piece is uniformly provided on the stage 180, whereas if the measured waveform is not within the desired (or alternatively, predetermined) reference range, the controller determines that the test piece is not uniformly provided on the stage 180.

Figure 5A:
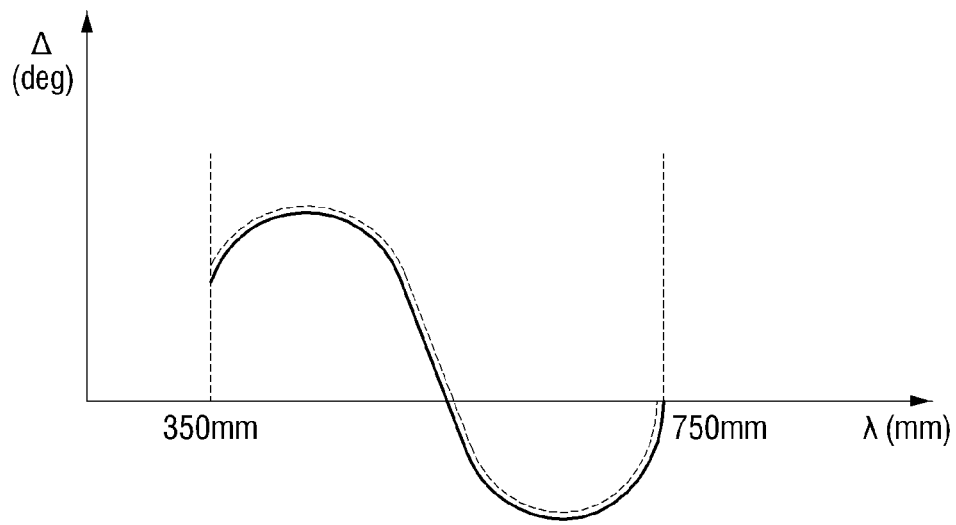
FIGS. 5A and 5B are diagrams explaining the principle of determining uniformity of a pattern formed on a substrate, and illustrates examples, in which a measured wave is similar to and is different from a pre-stored wave.
Figure 5B:
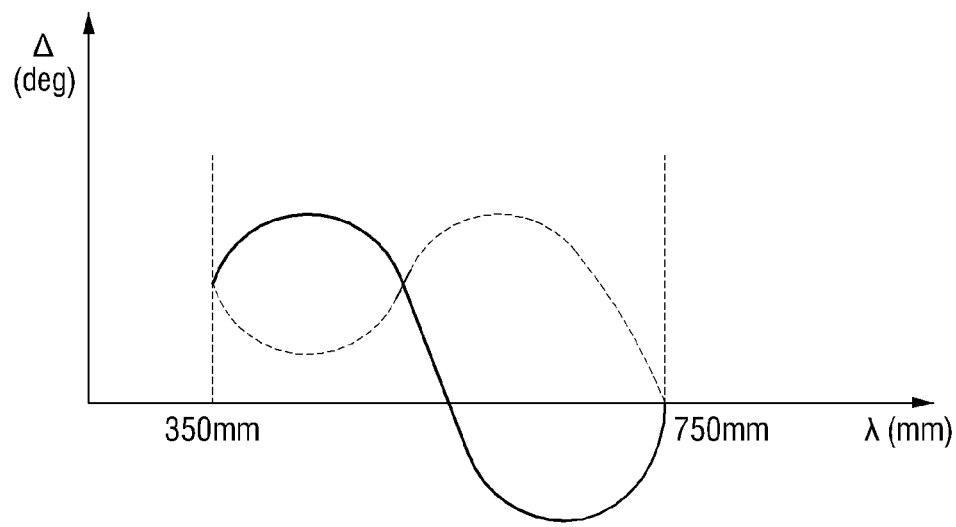

FIGS. 5A and 5B are diagrams explaining the principle of determining the uniformity of the pattern P formed on the substrate 190. In the graphs of FIGS. 5A and 5B, the wavelength of incident polarized light is presented on a horizontal axis, and a delta value measured by a detector 140 is presented on a vertical axis.

Referring to FIG. 5A, the measured waveform and the desired (or alternatively, the pre-stored) reference waveform are similar to each other, and it is estimated that the pattern P on the substrate 190 is uniform. Referring to FIG. 5B, the measured waveform and the desired (or alternatively, the pre-stored) reference waveform are different from each other, and it is estimated that the pattern P on the substrate 190 is not uniform.

As described above, the ellipsometer for detecting a surface measures the uniformity of the pattern P formed on the substrate 190 through performing measurement in a surface unit rather than in a point unit and comparing the measured waveform with the desired (or alternatively, pre-stored) reference waveform.

In this case, in accordance with the shape and the uniformity of the pattern P that is formed on the surface of the substrate 190, the vibration direction of the wavelength of the reflected light differs when the light irradiated from the light source 110 is incident to and then is reflected from the pattern P. In order to measure a small change of the pattern P that is provided on the stage 180, it is required to make the light incident in a direction in which the change of the waveform is large and to compare similarities between the waveforms having a large change width.

Figure 6A:
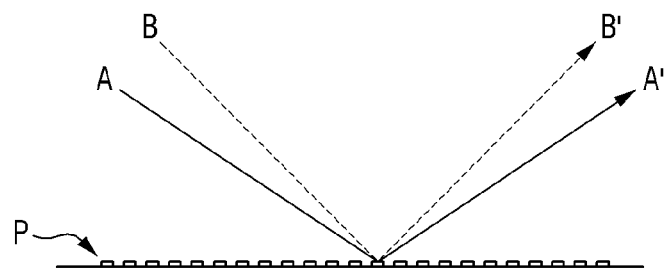
FIGS. 6A to 6C are views explaining output values of polarized light detected by a detector according to incident directions of light.
Figure 6B:
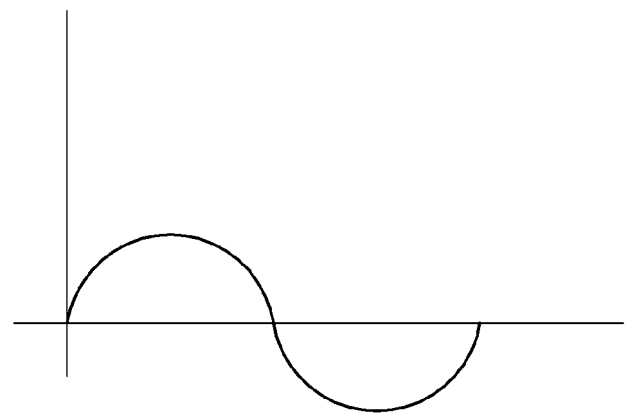
Figure 6C:
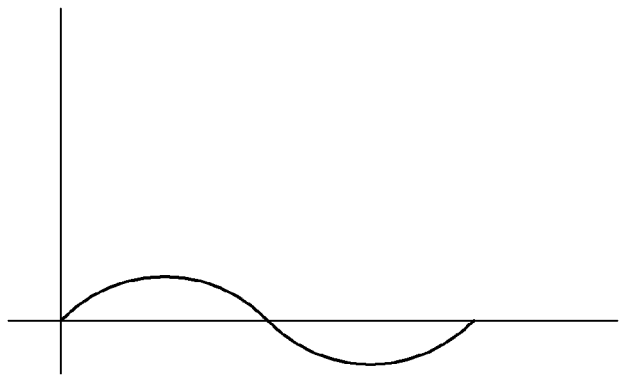

More specifically, in the case of comparing a case where light is incident in direction A with a case where light is incident in direction B as shown in FIG. 6A, when the light is incident in the direction A, the amount of received light detected by the detector 140 may differ even if the same measurement area is measured as when the light is incident in the direction B, and thus the waveform to be analyzed by the controller may also differ. For example, as illustrated in FIGS. 6B and 6C, because the output value may be larger when the light is incident in the direction A than when the light is incident in the direction B, monitoring the pattern P may be performed by making the light incident in the direction A.

As a result, in order to monitor the pattern P more precisely, the light of the ellipsometer may be configured to be incident in the direction in which the change of the waveform operated by the controller becomes large. For example, an optimum condition may be found by adjusting the incident angle and azimuth angle of the light irradiated from the light source 110.

Hereinafter, the concept of the incident angle and the azimuth angle will be described with reference to the accompanying drawings, and the operation principle of the driver 150 accommodating the change of the azimuth angle will be described in detail.

Figure 7A:
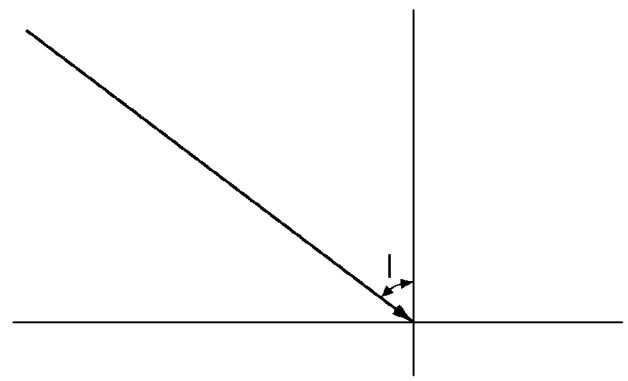
FIG. 7A is a view explaining an incident angle that is an angle with the normal of incident light.
Figure 7B:
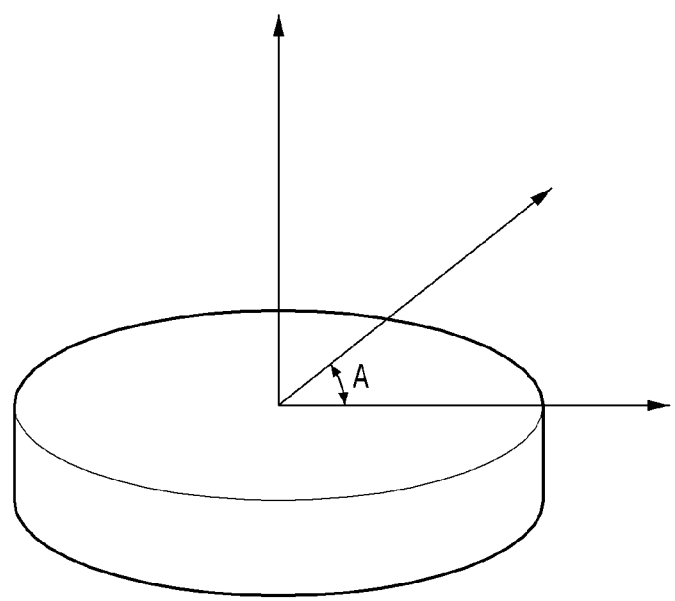
FIG. 7B is a view explaining an azimuth angle that is an angle against a reference line in a horizontal direction.

FIG. 7A is a view explaining an incident angle that is an angle with the normal of incident light, and FIG. 7B is a view explaining an azimuth angle A that is an angle against a reference line in a horizontal direction. In particular, the incident angle I is an angle with respect to the normal of incident light and the azimuth angle A is an angle between a projected line and a reference line on a horizontal plane.

If a target object to be measured has a specific shape, which is not a circular shape, the geometrical shape change of a target area projected onto the detector 140 in accordance with the change of the incident angle I can be compensated for by an optical method, but the geometrical shape changed in accordance with the change of the azimuth angle A may not to be compensated for. Accordingly, as the azimuth angle A changes, the effective measurement region of a region to be measured (hereinafter referred to as a measurement region) also may change.

Figure 8A:
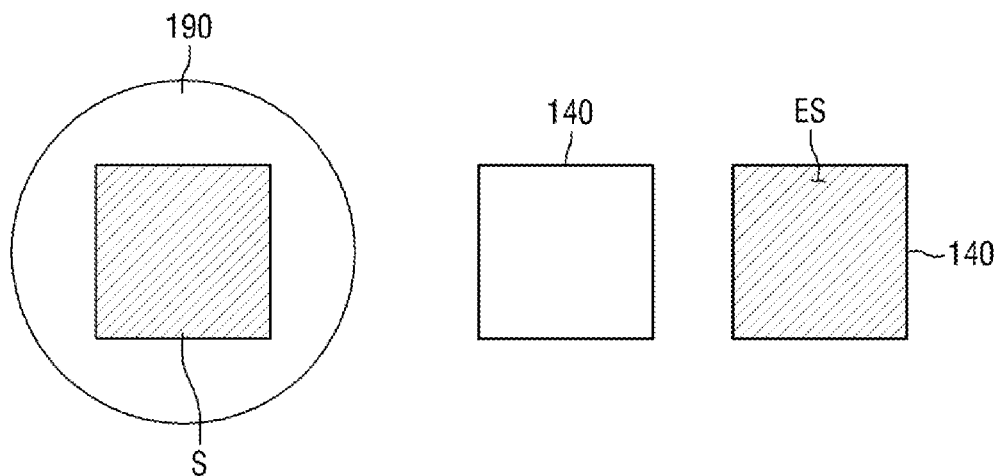
FIGS. 8A and 8B are views explaining the principle, in which an effective area that is measured by a detector differs as the azimuth angle of light that is irradiated from a light source is changed.
Figure 8B:
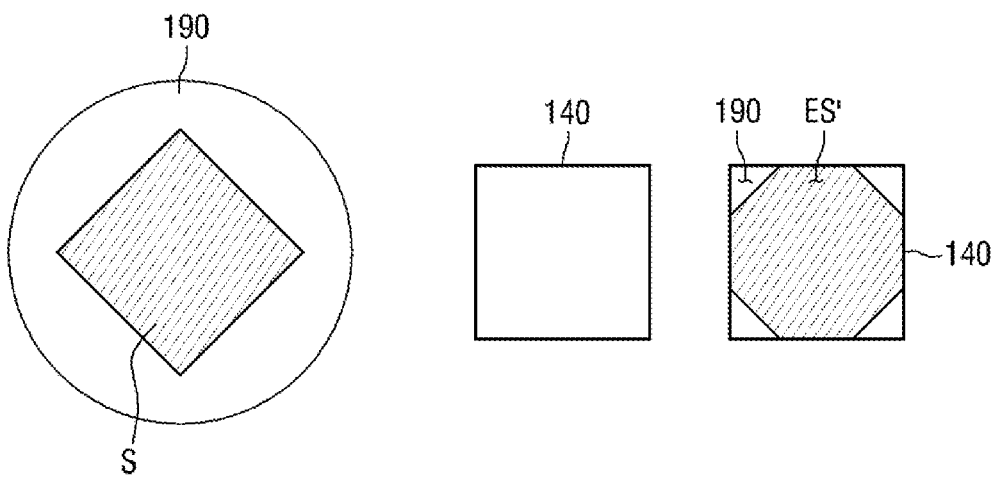

FIGS. 8A and 8B are views explaining the principle, in which an effective measurement region ES projected onto the detector 140 changes as the azimuth angle A of light irradiated from the light source 110 changes. FIG. 8A illustrates an effective measurement region ES of the substrate 190 projected onto the detector 140 when rotation of a measurement region R with respect to the detector 140 is set to 0° in the direction of the azimuth angle A. FIG. 8B illustrates an effective measurement region ES' of the substrate 190 projected onto the detector 140 when the measurement region R is rotated with respect to the detector 140 in the direction of the azimuth angle A.

For convenience of explanation, FIGS. 8A and 8B illustrate example cases where the region to be measured and the detection region of the detector 140 are in a square shape.

Referring to FIG. 8A, if the azimuth angle A between the detector 140 and the measurement region in a general ellipsometer for detecting a surface is 0°, the measurement region S and the effective measurement region ES, which is the measurement region projected onto the detector 140, are equal to each other.

Referring to FIG. 8B, if the azimuth angle A of the light irradiated from the light source 110 rotates, the measurement region S projected onto the detector 140 also rotates, and only a portion of the measurement region to be measured is projected onto the detector 140.

As a result, in the case of FIG. 8B, a separate measurement should be performed to obtain the waveform with respect to the measurement region S in addition to the effective measurement region ES', and this may cause the measurement time to be lengthened.

In the ellipsometer for detecting a space according to an example embodiment of the present inventive concepts, the driver 150 is configured to measure the physical properties of the target object without loss of measurement area and/or measurement speed even if the azimuth angle A of the measurement region S rotates.

For example, the controller changes the azimuth angle A when the azimuth angle A of the light irradiated from the light source 110 or the azimuth angle A of the substrate 190 rotates, and controls the driver 150 to rotate the detector 140 in accordance with the azimuth angle A at which the light rotates. The driver 150 rotates the detector 140 with respect to the optical axis while maintaining the optical axis of the detector 140 using the controller. As a result, even if the azimuth angle A of the light or the substrate 190 rotates, the physical properties of the pattern P formed on the substrate 190 can be measured without any substantial loss of measurement area and/or measurement speed.

Next, an ellipsometer for detecting a surface according to another example embodiment of the present inventive concepts will be described in detail.

An ellipsometer for detecting a surface according to another example embodiment of the present inventive concepts may include a light source irradiating a substrate with light, a polarization unit polarizing the light irradiated from the light source and analyzing the polarized light, a detector measuring a light quantity of the polarized light, which passes through the polarization analyzer, through a sensor, a memory storing information with regard to a pattern formed on the substrate, and a controller determining pixels that can be sensed by the sensor or an activated sensing region of the sensor based on information stored in the memory.

Further, the polarization unit may include a polarization generator polarizing the light irradiated from the light source and outputting the polarized light to the substrate, and a polarization analyzer provided to analyze a change of a vibration direction of the polarized light reflected from the substrate and to divide the polarized light reflected from the substrate into coordinate components.

Figure 9:
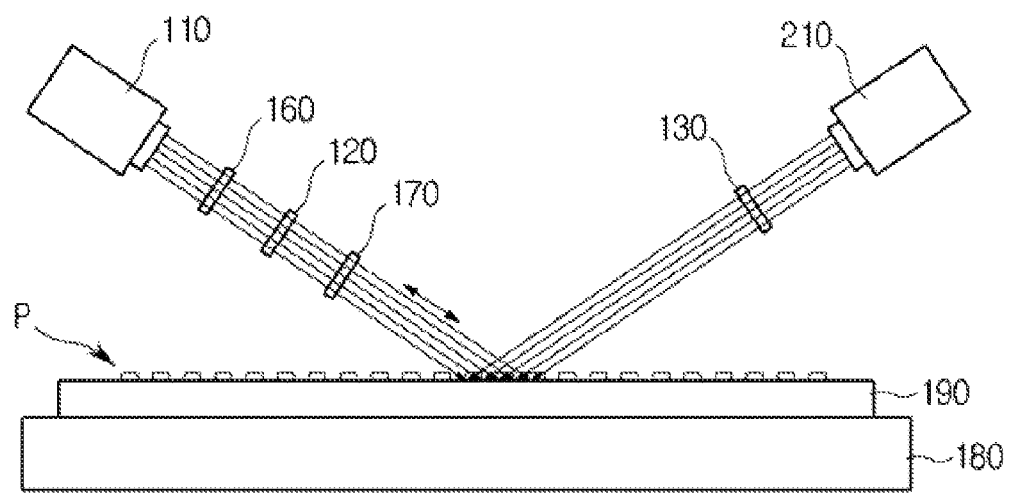
FIG. 9 is a view illustrating an example of the structure of an ellipsometer for detecting a surface, in which masking of a measurement region becomes possible, according to another example embodiment of the present inventive concepts.

FIG. 9 is a view illustrating an example of the structure of an ellipsometer for detecting a surface, in which masking of a measurement region S becomes possible, according to another example embodiment of the present inventive concepts.

Referring to FIG. 9, an ellipsometer for detecting a surface according to another example embodiment of the present inventive concepts includes a light source 110, a polarization generator 120, a polarization analyzer 130, a detector 210, a memory (not illustrated), and a controller (not illustrated). The ellipsometer for detecting a surface according to this example embodiment further includes a monochrometer 160 provided between the light source 110 and the polarization generator 120 and a compensator 170 provided between the polarization generator 120 and a substrate 190.

A stage 180 may move the substrate 190 to a place where the substrate 190 is to be attached by adjusting the stage 180. The ellipsometer for detecting a surface according to this example embodiment adopts a masking technology to measure the physical properties of the pattern P formed on the substrate 190 more promptly and accurately. Hereinafter, for convenience of explanation, explanation will be made with respect to the case where the uniformity of the pattern, for example, the pattern P as illustrated in FIG. 2, is measured.

The functions of the light source 110, the monochrometer 160, the polarization generator 120, the compensator 170, and the polarization analyzer 130 are the same as or substantially similar to those of the ellipsometer for detecting a surface as illustrated in FIG. 1. Accordingly, the detector 210, the memory, and the controller, which are the distinctive features of the ellipsometer according to this example embodiment, will be described in detail.

The detector 210 is a device for measuring the quantity of light, and more specifically, is a device which receives spectral light from a spectrometer, generates charges corresponding to the amount of received light, and outputs the charges as a received light output.

In the detector 210 according to this example embodiment, a 2D area image sensor, for example, a CMOS (Complementary Metal-Oxide Semiconductor) or a CCD (Charge Coupled Device), to which the masking technology can be applied, may be used.

Hereinafter, for convenience of explanation, a CCD sensor, to which the masking technology can be applied, is used to explain the masking function.

The masking technology is a technology which does not store data by masking of a portion that is not to be measured. The detector 210 according to this example embodiment does not acquire data of a masked region, and thus can shorten data transfer time through reduction of the amount of data to be actually measured.

The masked region may be determined by two methods, for example, by calculation and by actual measurement. The CCD according to this example embodiment may adopt only one or both of the two methods.

The calculation method can be adopted in the case where information on the measurement region S of an object is given in advance. For example, in the case of measuring the uniformity of a pattern P formed on a wafer in a semiconductor process, information on an active region where the pattern P is formed and an inactive region where the pattern P is not formed may be pre-stored in the memory.

In this case, the controller can determine in advance unit elements that will sense data and unit elements that will not sense data among various unit elements provided in the CCD based on the data regarding the active region and the inactive region pre-stored in the memory, and controls only the unit elements that will sense the data. Thus, the controller controls the operation of the stage 180 so that only specific unit elements can sense the data.

The actual measurement method can be adopted in the case where references values to be derived with respect to a specific measurement object are given.

For example, through the actual measurement, masking map data for the active region where the pattern P is formed and the inactive region where the pattern P is not formed is formed, reference information for pixels of the active region and the inactive region are prepared, and the uniformity of the pattern P is measured through determination of the masking region using the data.

Figure 10:
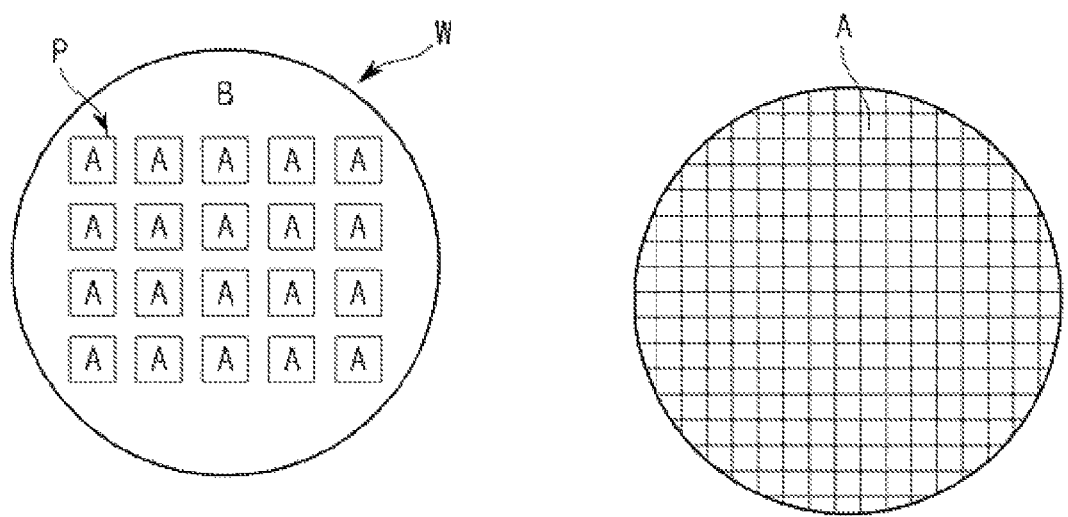
FIG. 10 is a view explaining the principle of determining a masking region through an actual measurement method.

FIG. 10 is a view explaining the principle of determining a masking region through an actual measurement method.

Referring to FIG. 10, in the memory, formation information on the active region and the inactive region of the pattern P, both of which are provided on the wafer W, output information on the active region where the pattern P is prepared, and output information on the inactive region where the pattern P is not prepared are pre-stored as colors A and B.

In order to measure the uniformity of the pattern P prepared on the wafer W, the controller controls only the unit elements of the CCD configured to sense color A, and as a result, the data on the inactive region is masked.

The controller extracts the optical properties of the pattern P through analysis of the waveform of the voltage and/or current, which are detected by the detector 210. For example, the controller controls the unit elements of the CCD based on the data pre-stored in the memory so that the detector 210 acquires only the information on color A, and measures the uniformity of the pattern P through comparison and analysis of the acquired information and the pre-stored formation information of the active region and the inactive region.

As a result, because the masking function is applied and the data on the masking region is not stored, the amount of actual measurement data is reduced, thereby shortening data transfer time.

Because a principle of analyzing the waveform of the voltage and/or current through the controller is the same as or substantially similar to the principle described above, duplicate explanation thereof will be omitted.

Next, an ellipsometer for detecting a surface according to still another example embodiment of the present inventive concepts will be described in detail.

The ellipsometer for detecting a surface according to still another example embodiment of the present inventive concepts is in the form where the ellipsometer for detecting a surface illustrated in FIG. 1 and the ellipsometer for detecting a surface illustrated in FIG. 9 are combined. The ellipsometer for detecting a surface according to this example embodiment includes a light source 110, a polarization generator 120, a polarization analyzer 130, a detector 210, a driver 150, a memory (not illustrated), and a controller. The ellipsometer for detecting a surface according to this example embodiment may further include a monochrometer 160 and a compensator 170.

The principle of the light source 110, the polarization generator 120, the polarization analyzer 130, the detector 210, the driver 150, and the memory is the same as or substantially similar to those described above, and according to the control of the controller, the ellipsometer for detecting a surface according to this example embodiment of may have both the characteristics of the ellipsometer for detecting a surface illustrated in FIG. 1 and the characteristics of the ellipsometer for detecting a surface illustrated in FIG. 9.

Figure 11:
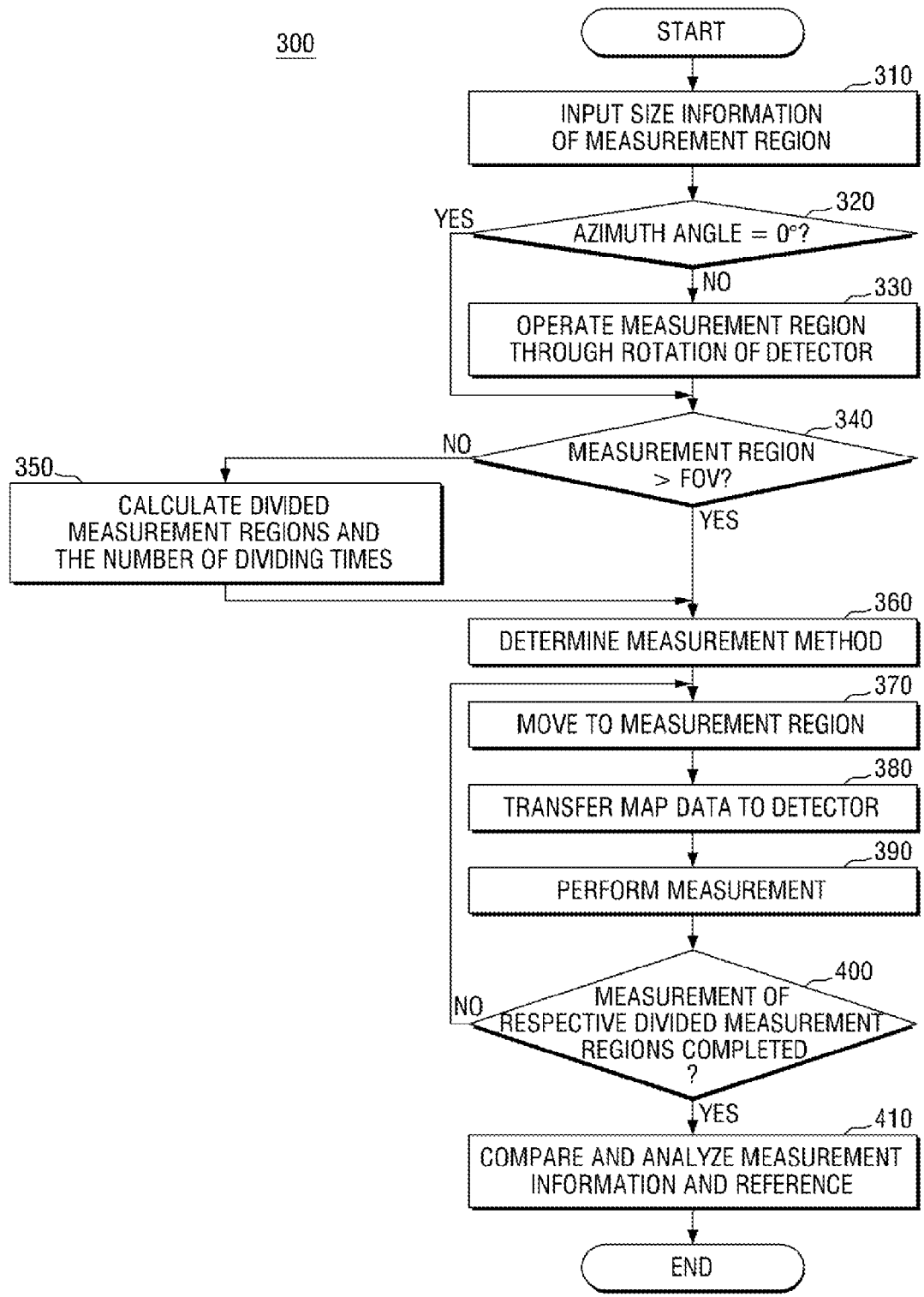
FIG. 11 is a flowchart illustrating a control process performed by a controller according to an example embodiment of the present inventive concepts.

FIG. 11 is a flowchart illustrating a control process performed by a controller according to an example embodiment of the present inventive concepts.

Referring to FIG. 11, in the case of measuring a measurement region S through the ellipsometer for detecting a surface according to this example embodiment, the controller first collects data on size information of the measurement region S (310). The data on the size information of the measurement region S may include a desired (or alternatively, pre-stored) data in accordance with a user's input.

If the data on the size information of the measurement region S is collected, the controller determines whether to rotate an azimuth angle A between the measurement region S and a detection region of a detector (not illustrated) (320).

If the azimuth angle A rotates by an angle other than 0° (if the detector rotates by a specific azimuth angle A of θ with respect to the measurement region S), the controller operates the measurement region S of the substrate 190 in accordance with the rotation of the detector (330).

If the azimuth angle A rotates by 0°, the controller performs the next operation without rotating the detector.

After the operation of the rotation of the azimuth angle A, the controller compares the measurement region S with a FOV (Field Of View) region of the detector. If the measurement region S is larger than the FOV region of the detector, the controller calculates divided measurement regions S and the number of dividing times, whereas if the measurement region S is not larger than the FOV region of the detector, the controller performs the next control process (340 and 350).

After the operation of the measurement region S, the controller determines measurement method(s) for the measurement region S in accordance with determination method(s) of the masking region (360).

As described above, the masking region is determined by, for example, calculation method and by actual measurement (S360).

If the masking map data by the calculation is pre-stored, the controller measures the measurement region S according to the calculation method, whereas if the masking map data by the actual measurement is pre-stored, the controller measures the measurement region S according to the actual measurement method.

If the masking map data according to the two methods are pre-stored, the controller may measure the measurement region S by selectively applying the two methods. In this case, the controller may determine the measurement method in accordance with a user's setting of the measurement method or in a desired (or alternatively, predetermined) order.

If the measurement method is determined, the detector moves to a measurement position of at least one desired (or alternatively, predetermined) divided measurement region S (370).

In accordance with the movement of the detector, the masking map data of the measurement region S is transferred to the detector, and the detector collects the data of the active region based on the transferred masking map data (380 and 390).

For example, in the case of the measurement method by the calculation, the controller determines in advance unit elements that will sense data and unit elements that will not sense data among various unit elements provided in the CCD based on the data regarding the active region and the inactive region pre-stored in the memory, and controls only the unit elements that will sense the data.

In the case of the measurement method by the actual measurement, the controller operates to collect the data of the active region through determination of the data to be sensed by the elements provided in the CCD using the masking map of the active region and the inactive region pre-stored in the memory as references.

If the data of all the divided measurement regions S in the above-described method are collected, the controller can determine whether the pattern P is uniformly formed on the measurement region S through comparison of the data of the measurement region S with respect to a desired (or alternatively, pre-stored) reference value of the measurement region S (400 and 410).

Because the principle of determining the uniformity of the pattern P is the same as that as described above, the duplicate explanation thereof is not repeated omitted.

Although various example embodiments have been described for illustrative purposes, those skilled in the art will appreciate that various modifications, additions and substitutions are possible, without departing from the scope and spirit of example embodiments as disclosed in the accompanying claims.

What is claimed is:

1. An ellipsometry method for detecting a surface monitoring physical properties of a substrate, comprising:
    irradiating a measurement region of the substrate with a first light, the first light being a polarized light;
    determining whether to rotate a detector by an azimuth angle between the measurement region and a detection region of the detector, the azimuth angle being an angle at which the substrate rotates from a reference line in a horizontal direction;
    rotating the detector about an optical axis of a second light incident to the detector by the azimuth angle, while the irradiated first light being not rotated, the second light being reflected from the substrate;
    passing the second light through a polarization analyzer; and
    measuring, by the detector, a light quantity that passes through the polarization analyzer.

2. The ellipsometry method of claim 1, wherein the rotating the detector comprises rotating the detector using the optical axis as a rotation axis while maintaining the optical axis.

3. The ellipsometry method of claim 1, further comprising:
    collecting size information of the measurement region before irradiating the first light.

4. The ellipsometry method of claim 3, further comprising:
    comparing the measurement region with a FOV (Field Of View) region of the detector after collecting the size information of the measurement region.

5. The ellipsometry method of claim 4, further comprising:
    determining a masking region that is a non-measurement region of the measurement region after comparing the measurement region with the FOV region.

6. The ellipsometry method of claim 1, further comprising:
    changing a phase of the first light after irradiating the first light.

7. The ellipsometry method of claim 1, wherein the detector comprises a two-dimensional sensor for detecting a surface, and the two-dimensional sensor is a CMOS (Complementary metal-oxide semiconductor) or CCD (charged coupled device) type sensor.

8. An ellipsometry method for monitoring physical properties of a substrate, comprising:
    preparing the substrate on which an active region and an inactive region are defined, the active region being a region where a pattern is formed, and the inactive region being a region where the pattern is not formed;
    irradiating the substrate with a first light, the first light being a polarized light;
    detecting a second light reflected from the active region;
    determining whether to rotate a detector by an azimuth angle between the active region and a detection region of the detector using the second light, the azimuth angle being an angle at which the substrate rotates from a reference line in a horizontal direction;
    rotating the detector about an optical axis of the second light incident to the detector by the azimuth angle, while the irradiated first light being not rotated;
    passing the second light through a polarization analyzer; and
    measuring, by the detector, a light quantity that passes through the polarization analyzer.

9. The ellipsometry method of claim 8, further comprising:
    storing information on the active region and information on the inactive region.

10. The ellipsometry method of claim 9, wherein output information on the active region is stored as a first color, and output information on the inactive region is stored as a second color different from the first color.

11. The ellipsometry method of claim 10, wherein the detector detects the second light by sensing the first color.

12. The ellipsometry method of claim 8, wherein the detector comprises a two-dimensional sensor for detecting a surface, and the two-dimensional sensor is a CMOS (Complementary metal-oxide semiconductor) or CCD (charged coupled device) type sensor.

* * * * *